United States Patent
Worland

[11] Patent Number: 6,019,781
[45] Date of Patent: Feb. 1, 2000

[54] ROTATOR CUFF NEEDLE

[76] Inventor: Richard L. Worland, 635 Walsing Dr., Richmond, Va. 23229

[21] Appl. No.: 09/173,064
[22] Filed: Oct. 16, 1998
[51] Int. Cl.[7] .................................................. A61B 17/06
[52] U.S. Cl. .......................................... 606/222; 606/223
[58] Field of Search ................... 606/222, 223, 606/224, 225, 226; 289/16

[56] References Cited

U.S. PATENT DOCUMENTS

| | | | |
|---|---|---|---|
| 279,693 | 6/1883 | Blinn | 606/222 |
| 312,408 | 2/1885 | Wackerhagen | 606/222 |
| 818,152 | 4/1906 | Edwards | 606/222 |
| 4,527,564 | 7/1985 | Eguchi et al. | 128/339 |
| 5,064,411 | 11/1991 | Gordon, III | 604/48 |
| 5,089,012 | 2/1992 | Prou . | |
| 5,222,977 | 6/1993 | Esser | 606/223 |
| 5,476,480 | 12/1995 | Matsutani et al. . | |

OTHER PUBLICATIONS

ARTHROTEK Brochure, date unknown.

*Primary Examiner*—Michael Buiz
*Assistant Examiner*—Tina T. D. Pham
*Attorney, Agent, or Firm*—Laubscher & Laubscher

[57] ABSTRACT

A surgical needle to simplify rotator cuff muscle tendon surgery and reduce the cost thereof, has a semi-circular body including a proximal end portion terminating in a point, a blunt distal end, an intermediate portion, and through-openings at each end. The proximal end of the needle is passed through bone and exits a trough formed therein. A suture from the rotator cuff tendon is passed through the proximal end through-opening. Thereafter, the needle is backed out from the bone, drawing the suture through the bone, following which the suture is tightened and secured to retain the rotation cuff tendon within the trough of the bone.

4 Claims, 2 Drawing Sheets

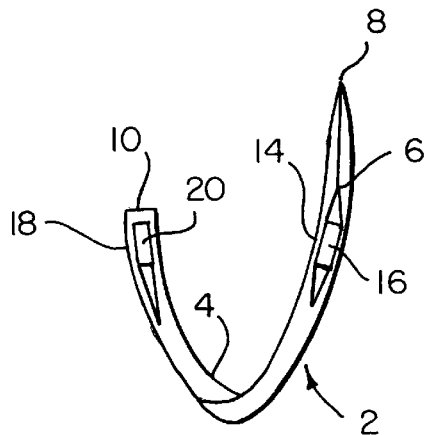 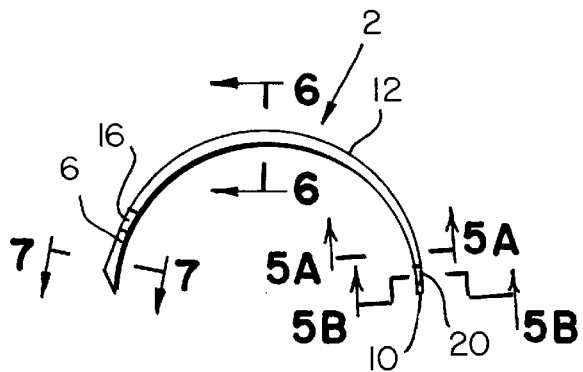 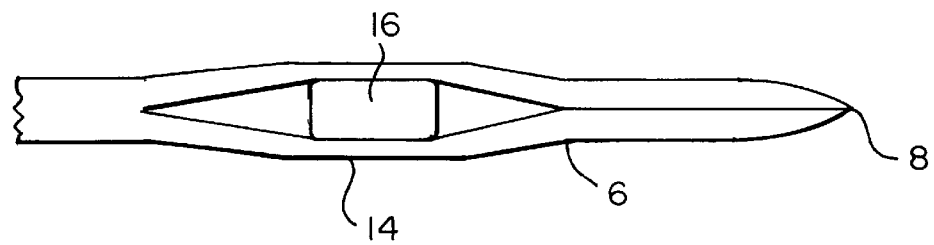 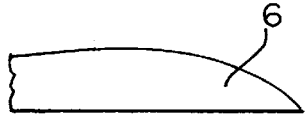 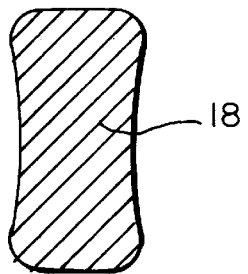
FIG. 1
FIG. 2
FIG. 3
FIG. 4
FIG. 5A

ROTATOR CUFF NEEDLE

BACKGROUND OF THE INVENTION

The present invention relates to a surgical needle and more particularly, a surgical rotator cuff needle strong enough to pass through bone, having a sharp point, and a hole at each end.

In rotator cuff surgery, a ruptured rotator cuff muscle tendon is sutured back into bone. Currently, rotator cuff surgery is difficult to perform, requiring orthopedic surgeons to use three complicated suture anchors. The suture anchors are secured into the bone below the trough. Then the attached sutures are passed through bone, up through a trough out in the bone, through the tendon, back through the trough, and out through the bone below the trough. Alternatively, the suture anchors are directly secured into the trough of the bone. Finally, a knot is tied which pulls the tendon into the slot. Each suture costs between two and five hundred dollars and the average surgeon uses three for each rotator cuff operation. The present invention was developed in order to simplify rotator cuff surgery and reduce the costs thereof.

BRIEF DESCRIPTION OF THE PRIOR ART

Surgical needles are well known in the patented prior art, as evidenced by U.S. Pat. Nos. 5,089,012 and 5,476,480. U.S. Pat. No. 5,089,012 discloses a rigid needle, wherein the needle and suture are joined by means of a filiform intermediate element, having a circular curvature, formed from a round body presenting a triangular end which is very sharp. It is designed to pass sutures forward through the sternum. However, the needle lacks a through-opening adjacent to its proximal end. Without this through-opening it cannot be used to advance a suture by pulling the needle backwards through a hole previously made by advancing the needle in forward fashion.

U.S. Pat. No. 5,476,480 discloses a curved surgical needle having an opening located adjacent to its distal end. The needle cannot penetrate bone because it does not have a sharp point. Additionally, it cannot be used to pass a suture by pulling the needle backwards through a hole previously made by advancing the needle in forward fashion, because it does not have a through-opening adjacent to its proximal end.

While the prior needles perform satisfactorily, they do not particularly lend themselves to rotator cuff surgery because they require the use of suture anchors and because of the difficulty in passing the needles through the bone. The present invention was developed in order to overcome these and other drawbacks of the prior needles by providing a new rotator cuff needle having a unique configuration.

SUMMARY OF THE INVENTION

Accordingly, it is a primary object of the present invention to provide a needle for rotator cuff surgery including an elongated curved body having a semi-circular configuration. The body has a proximal end portion terminating in a point, a blunt distal end portion, and an intermediate portion. Both end portions have flattened areas containing through-openings. When the needle pointed proximal end portion is passed into a bone and exits a trough formed therein, a suture from a rotator cuff tendon is passed through the first opening at the proximal end. The needle is then backed out from the bone to draw the suture through the bone. The suture is then tightened over a bone bridge and secured to retain the tendon within the trough of the bone.

The second opening at the distal end of the needle facilitates an alternate suturing procedure. A suture is passed through the second opening and the needle is pulled completely through the tendon, thus also pulling the suture through the tendon. The suture can be drawn through the bone using the forward opening described above and tightened and secured to retain the tendon in the trough.

According to a more specific object of the invention, the needle is formed of a hardened rigid metal and the proximal end portion has a generally triangular cross-sectional configuration terminating in the point, thereby facilitating penetration of and passage through a bone.

BRIEF DESCRIPTION OF THE FIGURES

Other objects and advantages of the invention will become apparent from a study of the following specification when reviewed in light of the accompanying drawings, in which:

FIG. 1 is a perspective view showing a rotator cuff surgical needle according to the invention;

FIG. 2 is a plan view of the rotator cuff surgical needle of FIG. 1;

FIGS. 3 and 4 are top and side views, respectively, of the pointed end of the rotator cuff surgical needle;

FIGS. 5A and 5B are cross-sectional views taken along lines 5A—5A and 5B—5B, respectively, of the needle of FIG. 2;

DETAILED DESCRIPTION

Figure 5B:
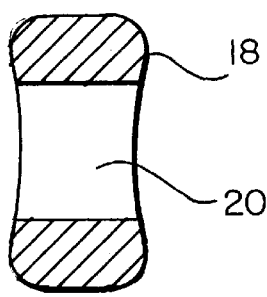
Figure 6:
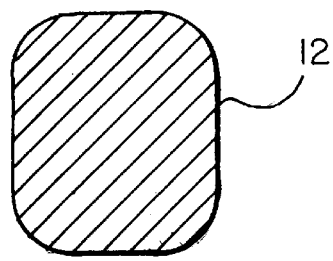
FIG. 6 is a sectional view of the immediate portion of the body of the rotator cuff surgical needle taken along line 6—6 of FIG. 2.

Referring first to FIGS. 1 and 2, there is shown a surgical needle 2 for rotator cuff surgery according to the invention. The needle 2 has an elongated body 4 curved into a generally semi-circular configuration, and includes a proximal end 6 terminating in a point 8, a blunt distal end 10, and an intermediate portion 12.

Figure 7:
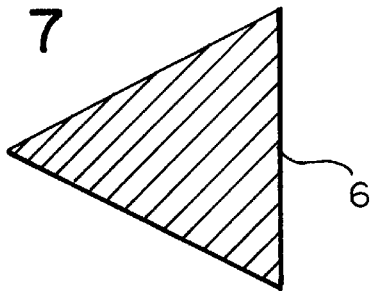
FIG. 7 is a sectional view of the tapering tip of the rotator cuff surgical needle taken along line 7—7 of FIG. 2.

As shown in FIGS. 3 and 4, the proximal end includes a flattened portion 14 containing a through-opening or through-hole 16. Beyond the opening 16, the proximal end has a triangular cross-sectional configuration (FIG. 7) and terminates in the top or point 8. This configuration facilitates penetration of bone material as will be developed in greater detail below.

The distal end 10 of the needle also includes a flattened portion 18 containing a through-opening 20 as shown in FIGS. 5A and 5B.

Between the proximal and distal ends of the needle, the intermediate portion 12 is provided. This portion is thickest at the midpoint of the needle, and gradually narrows in the direction of both ends. The needle is preferably formed of a hardened metal such as stainless steel, so that it does not flex or bend during penetration of a bone. The configuration of the proximal, intermediate, and distal portions as well as the semi circular configuration of the integral structure, enables the needle to more readily penetrate a bone as shown in FIG. 8.

Figure 8:
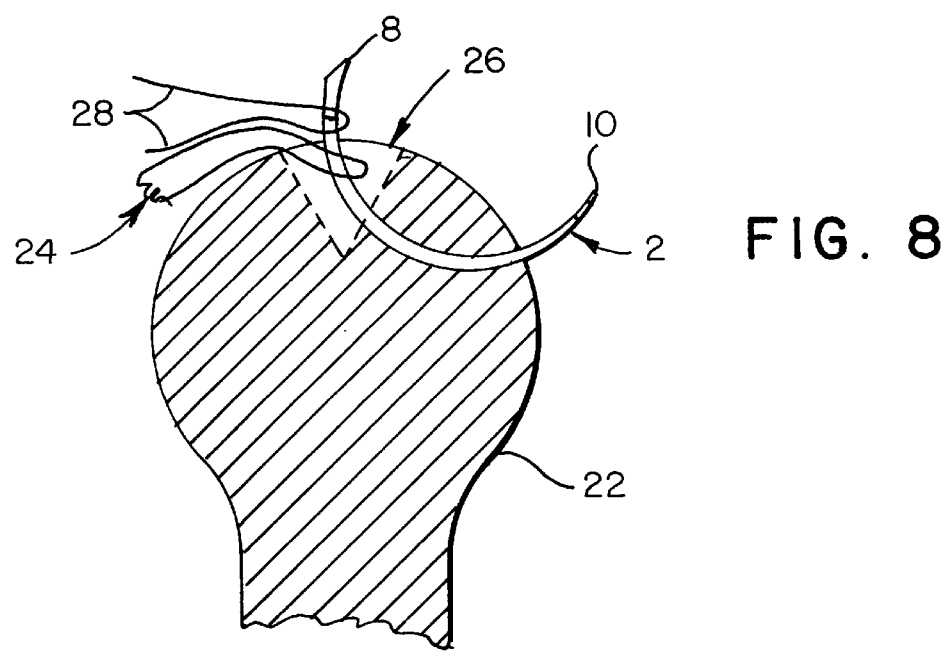
FIG. 8 is a partial sectional view of a bone showing use of the needle of the invention to attach a ruptured tendon to the bone.

More particularly, in FIG. 8 there is shown a bone 22, such as a shoulder, to which a ruptured rotator cuff tendon 24 is to be re-attached. A notch or trough 26 is chiseled into a desired location of the bone and the proximal end 6 of the needle is passed into the bone adjacent to the trough. Owing to the curvature of the needle, the proximal end emerges from the bone toward the bottom of the trough with the distal end remaining exterior of the bone. A suture 28 is passed through the opening 16 in the proximal end of the needle. The needle is then backed out of the bone, pulling the suture through the bone. One of the sutures may be connected with the tendon (such as by using a conventional needle pulled therethrough) and the free end of the suture is removed from the proximal opening 16 and pulled tight, thereby drawing the tendon into the trough, following which the suture is tied. Additional sutures can be tied in a similar manner to totally secure the tendon in the trough for healing.

The opening 20 in the distal end 10 of the needle 2 is used in an alternate procedure for securing a torn rotator cuff tendon. A suture 28 is passed through the opening 20 and then pulled through the tendon in a forward fashion. The needle thus can be used in place of a straight needle to fasten one end of the suture to the tendon. The suture is then unloaded from the distal end opening 20 and the proximal end of the needle is inserted through the bone as described above and as shown in FIG. 8 to subsequently pull the free end of the suture through the bone using the proximal opening 16.

While in accordance with the provisions of the patent statute, the preferred forms and embodiments have been illustrated and described. It will be apparent to those of ordinary skill in the art that various changes or modifications may be made without deviating from the inventive concepts set forth above.

What is claimed is:

1. A needle for rotator cuff surgery, comprising an elongated curved body including a proximal end portion terminating in a point, a blunt distal end portion, and an intermediate portion, said proximal end, distal end, and intermediate portions defining a semi-circular configuration, said proximal end portion being flattened and containing a first through-hole adjacent said pointed end, whereby when said needle pointed proximal end portion is passed into a bone and exits from a trough formed therein, a suture from a rotator cuff tendon is adapted to pass through said first through-hole, and when said needle is backed out from the bone, the suture is drawn by said first through-hole through the bone and the suture can be tightened and secured to retain the rotator cuff tendon within the trough of the bone.

2. A rotator cuff needle as defined in claim 1, wherein said blunt distal portion is flattened and contains a second through-hole whereby when a suture is passed through said second through-hole and said needle is passed completely through the rotator cuff tendon, the suture is pulled through the rotator cuff tendon for attachment thereto.

3. A rotator cuff needle as defined in claim 2, wherein said proximal end portion has a generally triangular cross-sectional configuration terminating in said point.

4. A rotator cuff needle as defined in claim 3, wherein said body is formed of a hardened rigid metal.

* * * * *